(12) United States Patent
Nakamura

(10) Patent No.: US 9,128,073 B2
(45) Date of Patent: Sep. 8, 2015

(54) NEEDLE MOVING DEVICE

(75) Inventor: Takafumi Nakamura, Kyoto (JP)

(73) Assignee: SHIMADZU CORPORATION, Kyoto-shi (JP)

( * ) Notice: Subject to any disclaimer, the term of this patent is extended or adjusted under 35 U.S.C. 154(b) by 666 days.

(21) Appl. No.: 13/381,194

(22) PCT Filed: Jul. 16, 2010

(86) PCT No.: PCT/JP2010/062077
§ 371 (c)(1),
(2), (4) Date: Dec. 28, 2011

(87) PCT Pub. No.: WO2011/007873
PCT Pub. Date: Jan. 20, 2011

(65) Prior Publication Data
US 2012/0109576 A1    May 3, 2012

(30) Foreign Application Priority Data

Jul. 17, 2009   (JP) ................................ 2009-169370

(51) Int. Cl.
*G01N 35/10* (2006.01)
(52) U.S. Cl.
CPC .......... *G01N 35/1011* (2013.01); *G01N 35/109* (2013.01)
(58) Field of Classification Search
CPC ................................................. G01N 35/1011
See application file for complete search history.

(56) References Cited

U.S. PATENT DOCUMENTS

| 4,602,196 | A * | 7/1986 | Matsui ......................... 318/603 |
| 6,799,291 | B1 * | 9/2004 | Kilmer et al. ................ 714/722 |
| 2002/0095974 | A1 * | 7/2002 | Gilson et al. .................. 73/1.74 |
| 2007/0012123 | A1 * | 1/2007 | Li et al. ....................... 73/863.01 |
| 2009/0226344 | A1 * | 9/2009 | Nishida et al. ................. 422/67 |

FOREIGN PATENT DOCUMENTS

| JP | 10-090279 A | 4/1998 |
| JP | 2785827 B2 | 8/1998 |
| JP | 2004-518134 A | 6/2004 |
| JP | 2006-189362 A | 7/2006 |
| WO | 02/059570 A1 | 8/2002 |

OTHER PUBLICATIONS

Definition of "fault", thefreedictionary.com, http://www.thefreedictionary.com/p/fault, (last accessed Oct. 23, 2014).*
International Search Report of PCT/JP2010/062077, mailing date Oct. 19, 2010.
Japanese Office Action dated Feb. 19, 2013, issued in corresponding Japanese Patent Application No. 2011-522871 (7 pp).

* cited by examiner

*Primary Examiner* — Timothy H Hwang
(74) *Attorney, Agent, or Firm* — Westerman, Hattori, Daniels & Adrian, LLP

(57) ABSTRACT

The invention provides a needle moving device which can detect a fault in a signal provided by a system controller to a performing device. An X-direction driving motor (4a) and a Y-direction driving motor (4b) in a driving portion (4) of an autosampler (1a) are provided with encoders (12a, 12b) for measuring moving distances of a needle (2) in respective directions from rotation numbers of the respective driving motors (4a and 4b). A determining portion (20) provided to a system controller (1b) locates a position of the needle (2) after the movement based on signals from the encoders (12a, 12b) and determines whether the position is a position of a designated sample vessel.

4 Claims, 2 Drawing Sheets

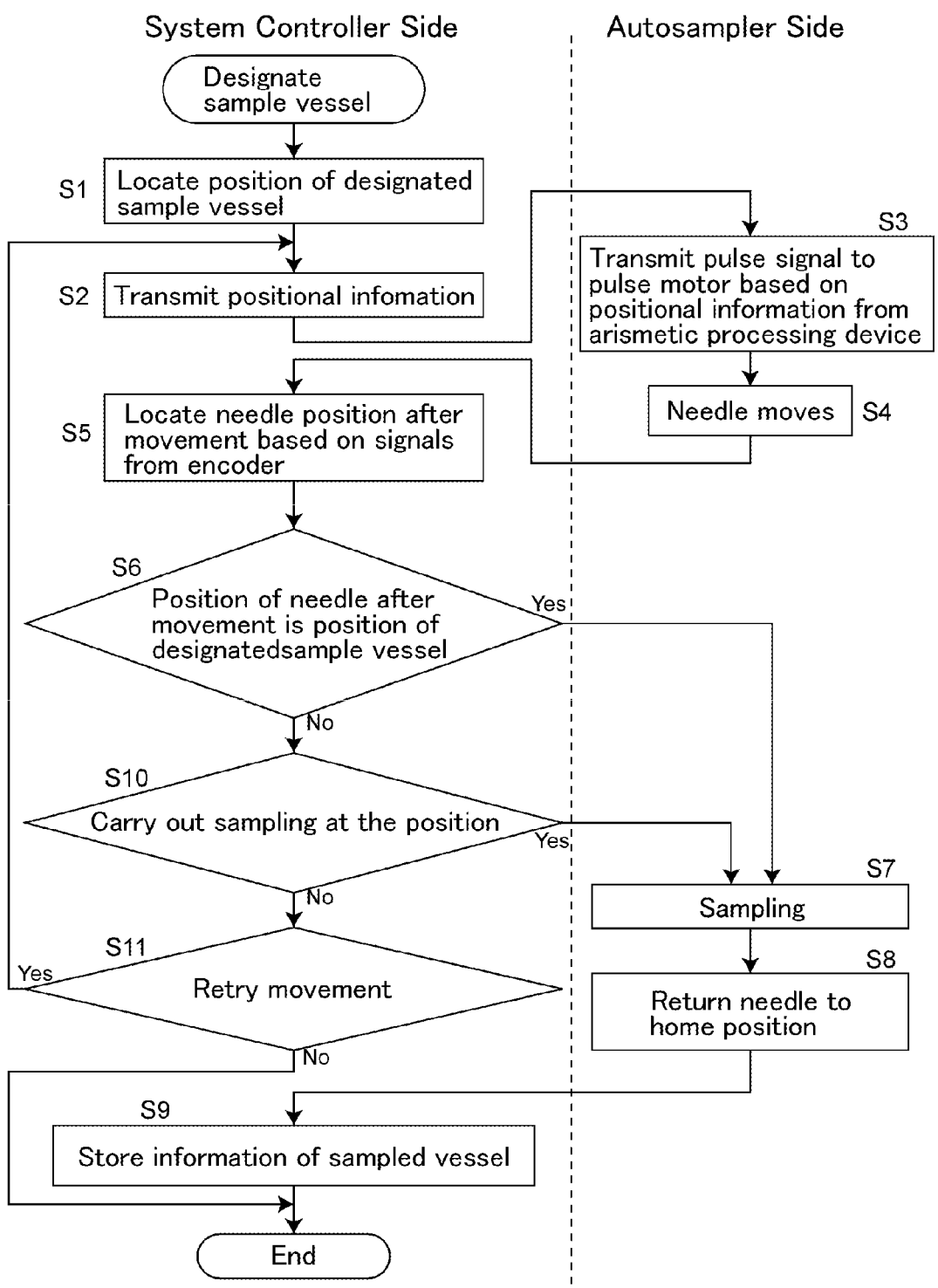

NEEDLE MOVING DEVICE

BACKGROUND OF THE INVENTION

1. Field of the Invention

The present invention relates to a needle moving device for moving a needle to a designated position. Such a needle moving device is applied to an autosampler for moving a needle to a position of a designated sample vessel to carry out sampling or a fraction collector for moving a needle to a predetermined position to drop an eluting solution from a liquid chromatograph to the position.

In the following description, the "needle" includes not only a needle-shaped member to be inserted into the sample vessel to take in a solution but also a needle just for dropping a solution.

2. Description of the Related Art

An autosampler and a fraction collector are for moving a needle to a designated position to take in or drop the sample. A needle moving device for moving the needle to the designated position is formed to move the needle in two directions orthogonal to each other in a horizontal plane and a vertical direction, in general. The needle moving device has a mechanism for moving the needle in each direction by driving pulse motors, and the needle moves a distance according to a pulse signal provided to each pulse motor in each direction (see Patent Document 1, for example).

Driving of the needle is generally controlled by a system controller. A personal computer, for example, which allows inputting, outputting, and displaying of information, is connected to the system controller, and an operator can control operation of a device including the needle moving device through the personal computer.

In the following description, a device such as the autosampler and the fraction collector for actually moving the needle to perform sampling or dispensing is defined as a performing device. On the other hand, a device such as the system controller connected to the performing device to control operation of the performing device is defined as an arithmetic processing device.

PRIOR-ART DOCUMENT

Patent Document

Patent Document 1: Japanese Patent No. 2785827

If the needle comes in contact with an obstacle and its movement is obstructed, the needle may not normally move to the position designated by the operator. In such a case, if operation such as sampling is carried out at a position where the needle stops, the sample vessel not intended to be sampled by the operator may be sampled or a tip end portion of the needle may poke at a position without the sample vessel and may bend. Therefore, if the needle has not moved to the position designated by the operator, it is important that this fact can be recognized.

In general, a pulse motor for moving the needle in each direction is provided with an encoder which can measure a moving distance of the needle from a rotation number of the pulse motor. In the performing device, a signal from the encoder is compared with a signal from the arithmetic processing device, and it is possible to determine whether the needle has moved normally based on whether both the signals coincide with each other.

However, the signal provided by the arithmetic processing device to the performing device may change into a different signal from the signal based on information inputted by the operator in some cases. If the needle moves according to the changed signal from the arithmetic processing device, the needle moves to a different position from the designated position while the performing device recognizes that the needle has moved normally. In other words, even if the signal provided by the arithmetic processing device to the performing device changes, it is impossible to detect this fault with the above-described method. Because the change of the signal to be provided to the performing device is not taken into consideration in the prior art, it is impossible to recognize that the signal to be provided to the performing device has changed.

SUMMARY OF THE INVENTION

It is therefore an object of the present invention to provide a needle moving device which can detect the fault when the signal provided by the arithmetic processing device to the performing device has changed.

The present invention includes: a performing device which includes a needle, a needle driving portion for moving the needle in at least a horizontal plane direction by driving of a motor, and an encoder provided to the motor to measure a moving distance of the needle based on a rotation number of the motor and which outputs a measurement signal produced by the encoder; an arithmetic processing device connected to the performing device to provide, to the performing device, a signal for moving the needle to a position designated by information inputted from outside; and a determining portion provided in the arithmetic processing device to receive the measurement signal produced by the encoder and outputted from the performing device, obtain a needle position after the movement, compare the needle position with a designated position, and determine whether both of them coincide with each other.

As a concrete embodiment, the needle driving portion includes an X-direction driving motor and a Y-direction driving motor for moving the needle in a direction X and a direction Y orthogonal to each other in the horizontal plane as the motor and respective encoders provided as the encoder to the X-direction driving motor and the Y-direction driving motor and the determining portion obtains the needle position in the horizontal plane based on the signals from both the encoders provided to the X-direction driving motor and the Y-direction driving motor and compares the position with the designated position.

The performing device preferably has a means (signal processing portion 6, in the embodiment) for detecting whether the needle after the driving has reached the designated position based on the measurement signal(s) from the encoder(s) and the signal provided by the arithmetic processing device. If the performing device cannot detect that the needle has reached the designated position, it is determined that the needle could not normally move due to a physical trouble such as contact with an obstacle. Accordingly, provided with such means in the performing device, it is possible to determine whether the fault in the movement of the needle to the designated position is caused by the performing device side or by the signal provided by the arithmetic processing device to the performing device.

In the needle moving device of the invention, because the determining portion for receiving the measurement signal produced by the encoder and outputted from the performing device, obtaining the position of the needle after the movement, and determining whether the position coincides with the designated position is provided to the arithmetic processing device, it is possible to determine whether the needle has moved normally on the arithmetic processing device side. In other words, the determining portion determines whether the movement of the needle is normal or abnormal based on the information before it is transmitted from the arithmetic processing device to the performing device. Therefore, if the signal from the arithmetic processing device to the performing device changes, it can be recognized as a fault.

BRIEF DESCRIPTION OF THE DRAWINGS

FIG. 2 is a flowchart showing operation of the embodiment.

DETAILED DESCRIPTION OF THE INVENTION

Figure 1:
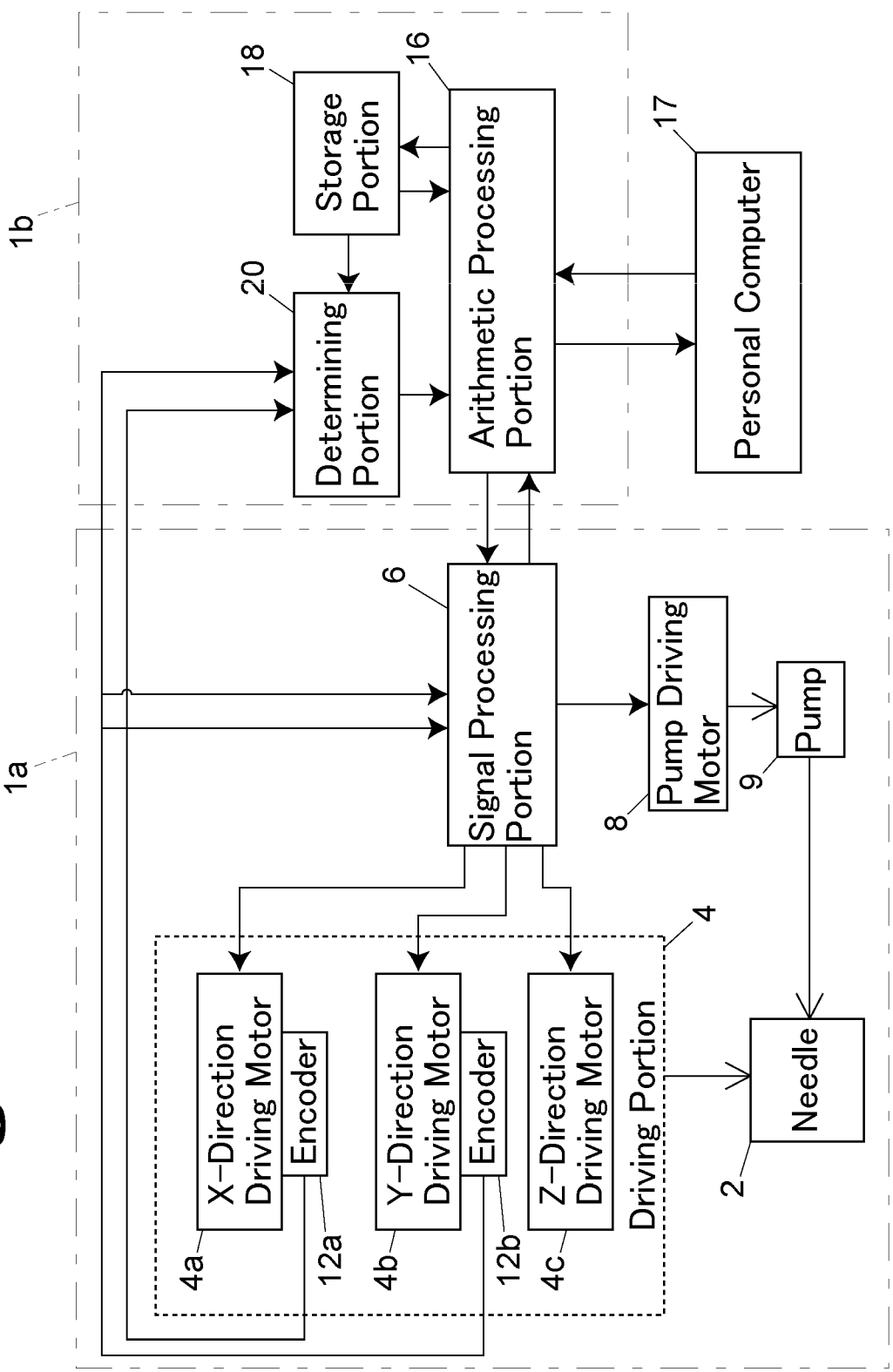
FIG. 1 is a block diagram showing a needle moving device according to an embodiment.

As an embodiment of the present invention, an example in which a needle moving device is applied to an autosampler will be described below with reference to FIG. 1.

The needle moving device is made up of an autosampler 1a as a performing device and a system controller 1b as an arithmetic processing device. To the system controller 1b, a personal computer 17 which is a device for carrying out input, output, and display of information is connected.

The autosampler 1a includes a needle 2. The needle 2 can be moved in directions in a horizontal plane and a vertical direction by a driving portion 4. A tip end of the needle 2 is connected to a syringe pump 9. A solution can be taken into and discharged from the tip end by actuating a pump driving motor 8 for driving a plunger of the syringe pump 9.

The driving portion 4 includes an X-direction driving motor 4a and a Y-direction driving motor 4b for moving the needle 2 in directions X and Y orthogonal to each other in the horizontal plane and a Z-direction driving motor 4c for moving the needle 2 in the vertical direction. The respective driving motors 4a, 4b, and 4c are pulse motors, for example, and are actuated according to pulse signals from a signal processing portion 6. The X-direction driving motor 4a and the Y-direction driving motor 4b are provided with encoders 12a and 12b, respectively. The encoders 12a and 12b can measure moving distances of the needle 2 in the respective directions from rotation numbers of the respective motors 4a and 4b. The signal processing portion 6 provides the pulse signals according to signals provided by the arithmetic processing device 1b to the respective driving motors 4a, 4b, 4c, and the pump driving motor 8.

The system controller 1b includes an arithmetic processing portion 16, a storage portion 18, and a determining portion 20.

The arithmetic processing portion 16 inputs information about sampling and inputted through a personal computer 17 and controls operation of the autosampler 1a according to the information. The information inputted by an operator through the personal computer 17 is a number of a sample vessel to be sampled, for example, and includes an order of the sampling of the sample vessels when there are a plurality of sample vessels. A plurality of sample vessels storing samples to be sampled in the autosampler are disposed on a rack provided below the needle 2, though they are not shown in the drawing. Information about positions where the respective sample vessels are disposed is inputted in advance through the personal computer 17, and the information is stored in, for example, the storage portion 18 of the system controller 1b or a storage device in the personal computer 17. In the embodiment, the information is stored in the storage portion 18 of the system controller 1b.

The arithmetic processing portion 16 locates the position of the designated sample vessel based on the information stored in the storage portion 18 and provides the positional information to the signal processing portion 6 of the autosampler 1a. If the plurality of sample vessels to be sampled and the order of the sampling are designated in advance, the position where the sample vessel to be sampled next is disposed is located according to the order, and the positional information is provided to the signal processing portion 6 of the autosampler 1a.

Signals from the encoders 4a and 4b are inputted to the determining portion 20 and the determining portion 20 obtains a position of the needle 2 after the movement from the signals, compares the obtained position of the needle 2 and the designated position with each other, and determines whether both the positions coincide with each other.

Information about the determination result from the determining portion 20 is inputted to the arithmetic processing portion 16 and the arithmetic processing portion 16 controls subsequent operation of the autosampler 1a based on the information.

FIG. 2 is a flowchart showing operation of the embodiment. The operation of the embodiment will be described in FIG. 2.

If the information of the sample vessel to be sampled is designated through the personal computer 17, the arithmetic processing portion 16 in the system controller 1b locates the position of the designated sample vessel from the information about the disposed position of the sample vessel stored in the storage portion 18 (step S1) and transmits the information to the autosampler 1a (step S2).

On the autosampler 1a side, the signal processing portion 6 provides pulse signals to the X-direction driving motor 4a and the Y-direction driving motor 4b based on the information provided by the arithmetic processing portion 16 (step S3) to move the needle 2 (step S4). At this time, the encoder 12a measures the moving distance of the needle 2 in the direction X from the rotation number of the X-direction driving motor 4a and the encoder 12b measures the moving distance of the needle 2 in the direction Y from the rotation number of the Y-direction driving motor 4b. The needle 2 is supposed to be returned to a home position before the signal for moving the needle 2 is provided by the system controller 1b.

After the movement of the needle 2, the determining portion 20 on the system controller 1b side locates the position of the needle 2 after the movement based on the signals from the encoders 12a and 12b (step S5) and determines whether the position of the needle 2 after the movement and the position of the designated sample vessel coincide with each other (step S6). The determination result by the determining portion 20 is inputted to the arithmetic processing portion 16.

If the position of the needle 2 after the movement coincides with the set position of the sample vessel, the arithmetic processing portion 16 provides a signal for carrying out the sampling to the autosampler 1a in this state. On the autosampler 1a side, the sampling is carried out according to the sampling starting signal from the arithmetic processing portion 16 (step S7). At the time of the sampling, the pulse signal is provided by the signal processing portion 6 to the Z-direction driving motor 4c so that the needle 2 moves down a certain distance and that the tip end portion is inserted into the sample vessel and, after the moving down of the needle 2, the pulse signal is provided to the pump driving motor 8 so that the syringe pump 9 takes in a predetermined amount of sample. After the end of the sampling, the needle 2 is returned to the home position (step S8). At this time, on the system controller 1b side, information about the sampled sample vessel is stored in the storage portion 18.

If the position of the needle 2 after the movement does not coincide with the set position of the sample vessel, the arithmetic processing portion 16 confirms with the operator whether to carry out the sampling at this position and asks the operator for decision by means of, for example, display on the display of the personal computer 17. To carry out the sampling in this state, the sampling starting signal is provided to the autosampler 1a to continue operations in steps S7 to S9. When the position of the needle 2 after the movement does not coincide with the set position of the sample vessel, it is highly likely that the movement of the needle 2 has not been carried out normally, and therefore, the sampling is not carried out usually. Therefore, the function of asking the operator for decision on whether to carry out the sampling at this position in such a case may not be provided.

If the position of the needle 2 after the movement does not coincide with the set position of the sample vessel and the sampling is not carried out at this position, whether to retry the movement of the needle 2 is determined (step S11). Decision on whether to retry the movement of the needle 2 is asked for by means of display of a confirmation message, for example, on the display of the personal computer 17. If the number of times of retries is set in advance, the retry is repeated the same number of times. To retry the movement of the needle 2, the positional information of the designated sample vessel is transmitted again from the arithmetic processing portion 16 to the autosampler 1a (step S2). This is because the fault in movement of the needle 2 detected by means of the determination by the determining portion 20 is caused by a fault in the signal provided by the system controller 1b to the autosampler 1a. By transmitting the signal from the system controller 1b to the autosampler 1a again, the trouble may be fixed in some cases.

Furthermore, the signals from the encoders 12a and 12b are inputted to the signal processing portion 6 as well in order to allow the signal processing portion 6 to locate the position of the needle 2 after the movement based on the signals from the encoders 12a and 12b and to confirm whether the position coincides with the positional information of the sample vessel provided by the arithmetic processing portion 16. If they do not coincide with each other, it is determined that the needle 2 could not move normally due to a physical trouble such as contact of the needle 2 with an obstacle. On the other hand, on the signal processing portion 6 side, it is possible to determine that the signal provided by the system controller 1b to the autosampler 1a was at fault when a fault in the movement of the needle 2 is detected based on the determination by the determining portion 20, even though the position of the needle after the movement based on the signals from the encoders 12a and 12b and the positional information of the sample vessel provided by the arithmetic processing portion 16 coincide with each other. In this manner, if not only the determining portion 20 but also the signal processing portion 6 can detect the fault in the movement of the needle 2 by utilizing the signals from the encoders 12a and 12b, it is possible to determine whether the fault in the movement of the needle 2 is caused by a change of the signal or by a physical trouble.

The above-described movement control of the needle 2 can be applied to a fraction collector which does not include a syringe pump and a pump driving motor and drops, from a tip end of a needle 2, an eluting solution from a liquid chromatograph as well.

Although the autosampler in which the needle 2 is moved down and the tip end of the needle 2 is inserted into the sample vessel in the sampling has been described in the above embodiment, the invention can be applied to the autosampler in which the rack where the sample vessels are disposed is moved up and down as well. In this case, the Z-direction driving motor 4c in the driving portion 4 is unnecessary.

DESCRIPTION OF REFERENCE NUMERALS 2 needle
4 driving portion
4a X-direction driving motor
4b Y-direction driving motor
4c Z-direction driving motor
6 signal processing portion
8 pump driving motor
9 syringe pump
12a, 12b encoder
16 arithmetic processing portion
17 personal computer
18 storage portion
20 determining portion

The invention claimed is:

1. A needle moving device comprising:
a performing device which includes
a needle,
a needle driving portion for moving the needle in at least a horizontal plane direction by driving of a motor, and
an encoder provided to the motor to measure a moving distance of the needle based on a rotation number of the motor, and
the performing device outputting a measurement signal produced by the encoder;
an arithmetic processing device connected to the performing device to transmit, to the performing device, a signal for moving the needle to a position;
a detector provided in the performing device, the detector being configured to detect whether, after the performing device moves the needle, a needle position after the movement based on the measurement signal from the encoder coincides with the signal transmitted to the performing device by the arithmetic processing device; and
a determining portion provided in the arithmetic processing device, the determining portion being configured to determine whether, after the performing device moves the needle, the needle position after the movement based on the measurement signal from the encoder coincides with a designated position that is inputted into the arithmetic processing device from outside,
wherein the needle moving device is configured to (i) compare the needle position after the movement with the designated position that is inputted into the arithmetic processing device from outside, and (ii) compare the needle position after the movement with the signal transmitted to the performing device by the arithmetic processing device, so as to determine whether a fault in the movement of the needle to the designated position is caused by the performing device or by the signal provided by the arithmetic processing device to the performing device.

2. The needle moving device according to claim 1, wherein the needle driving portion includes an X-direction driving motor and a Y-direction driving motor for moving the needle in a direction X and a direction Y orthogonal to each other in the horizontal plane as the motor, and respective encoders provided as the encoder to the X-direction driving motor and the Y-direction driving motor, and
the determining portion obtains the needle position in the horizontal plane based on the signals from both the encoders provided to the X-direction driving motor and the Y-direction driving motor and compares the needle position with the designated position.

3. The needle moving device according to claim 1, wherein when the needle position after the movement coincides with the position based on the signal transmitted to the performing device by the arithmetic processing device, then the fault in the movement of the needle is caused by the signal provided by the arithmetic processing device to the performing device.

4. The needle moving device according to claim 1, wherein when the needle position after the movement does not coincide with the position based on the signal transmitted to the performing device by the arithmetic processing device, then the fault in the movement of the needle is caused by the performing device.

* * * * *